United States Patent [19]

Marker

[11] Patent Number: 5,395,981
[45] Date of Patent: * Mar. 7, 1995

[54] HYDROCARBON CONVERSION BY CATALYTIC DISTILLATION

[75] Inventor: Terry L. Marker, Warrenville, Ill.

[73] Assignee: UOP, Des Plaines, Ill.

[ * ] Notice: The portion of the term of this patent subsequent to Nov. 3, 2010 has been disclaimed.

[21] Appl. No.: 112,299

[22] Filed: Aug. 27, 1993

Related U.S. Application Data

[63] Continuation-in-part of Ser. No. 902,179, Jun. 22, 1992, Pat. No. 5,258,560.

[51] Int. Cl.$^6$ .............................................. C07C 41/06
[52] U.S. Cl. .............................. 568/697; 203/DIG. 6; 568/694; 585/709; 585/446
[58] Field of Search .................. 568/697; 203/DIG. 6

[56] References Cited

U.S. PATENT DOCUMENTS

| | | | |
|---|---|---|---|
| 3,506,408 | 4/1970 | Kageyama et al. | 23/288 |
| 3,634,535 | 1/1972 | Haunschild | 260/677 A |
| 4,307,254 | 12/1981 | Smith, Jr. | 568/697 |
| 4,950,803 | 8/1990 | Smith, Jr. et al. | 568/697 |
| 5,118,871 | 6/1992 | Cikut et al. | 568/697 |
| 5,258,560 | 11/1993 | Marker | 568/697 |

*Primary Examiner*—Howard T. Mars
*Attorney, Agent, or Firm*—Thomas K. McBride; John F. Spears, Jr.

[57] ABSTRACT

Ethers suitable for use as high octane oxygenate additives for motor fuels or other compounds such as alcohols or alkylates are produced in a catalytic distillation process wherein a $C_4$-plus isoolefin(s) and an alcohol present in the catalytic distillation zone overhead stream are charged to a packed liquid-phase reaction zone containing an etherification catalyst before being recycled to the overall catalytic distillation zone. The effluent of the liquid-phase reactor is returned to the catalytic distillation zone at a point above the catalyst in this zone. The feed(s) to the process passes directly into the catalytic distillation zone, without passage through a prereactor, at a point located below a majority of catalyst bed in the catalytic distillation zone.

14 Claims, 1 Drawing Sheet

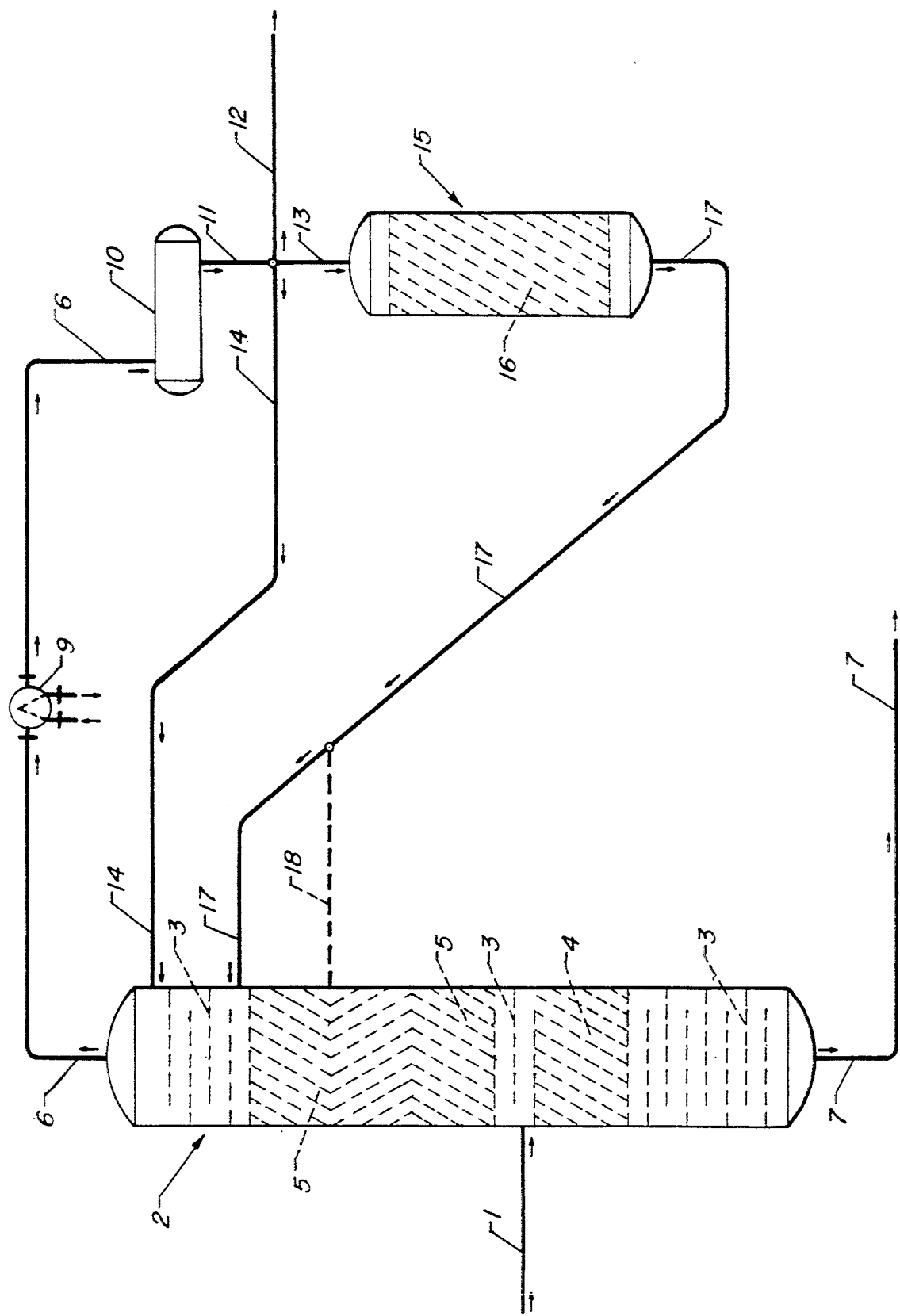

HYDROCARBON CONVERSION BY CATALYTIC DISTILLATION

CROSS REFERENCE TO RELATED APPLICATION

This application is a continuation-in-part of my prior application Ser. No. 902,179, filed 22 Jun. 1992, now U.S. Pat. No. 5,258,560.

FIELD OF THE INVENTION

The invention relates to a hydrocarbon conversion process useful in the etherification of isoolefins such as isobutylene. The invention also relates to the use of catalytic distillation to perform hydrocarbon conversion reactions. The invention specifically relates to a catalytic distillation process wherein isobutylene is reacted with methanol to form methyl tertiary butyl ether (MTBE).

RELATED ART

U.S. Pat. No. 3,506,408 to O. Kageyama et al. illustrates the use of catalytic distillation for carrying out reversible liquid phase reactions such as the production of acetals and esters by the reaction of two organic feed compounds. This reference teaches the use of ion exchange resin particles located on shelves with layers of packing such as Raschig rings located above the catalyst.

U.S. Pat. No. 3,634,535 to W. Haunschild and the references incorporated therein show that ethers, including methyl tertiary butyl ether, can be produced by catalytic distillation performed using catalyst located on distillation trays or with catalyst in the form of a resin coating on vapor-liquid packing used to promote distillation. Etherification by catalytic distillation using similar methods is also described in U.S. Pat. No. 4,950,803 issued to L. A. Smith et al.

The first commercial applications of catalytic distillation to etherification, as per the teachings of references such as U.S. Pat. No. 4,307,254 to L. A. Smith, Jr., in which the olefin feed stream is passed directly into the catalytic distillation column reportedly resulted in commercially unsatisfactory performance. This led to the adoption of a conventional liquid-phase "prereactor" upstream of the catalytic distillation zone, with the prereactor-catalytic distillation sequence becoming the standard commercial flow as shown in U.S. Pat. No. 5,118,871 issued to J. J. Cikut et al.

BRIEF SUMMARY OF THE INVENTION

The invention is a hydrocarbon conversion process for the production of ethers which provides good reactant utilization and ether yields without requiring a prereactor or an excessive amount of catalyst in the catalytic distillation zone. It has been found that the close-coupled reactor of the subject process need only contain 30 percent of the catalyst present in the prior art prereactor. The subject process can also be used in a variety of petrochemical applications including the production of diisopropyl ether and the hydration of olefins.

One broad embodiment of the invention may be characterized as a process for the production of ethers which comprises a process for the production of ethers which comprises the steps passing at least one $C_4$ to $C_6$ isoolefin and a $C_1$ or $C_2$ alcohol into a catalytic distillation zone maintained at mixed-phase conversion conditions which are effective to promote both the exothermic reaction of said isoolefin and alcohol to form a product ether and the fractional distillation of the contents of the catalytic distillation zone into an overhead vapor stream comprising said isoolefin and said alcohol and a bottoms stream which is rich in the product ether, with said isoolefin and said alcohol first entering the catalytic distillation zone at a point intermediate upper first and lower second catalyst retaining zones located within the catalytic distillation zone; condensing the overhead vapor stream to produce an overhead liquid and passing a first portion of the overhead liquid into the catalytic distillation zone as reflux; passing a second portion of the overhead liquid into an external reaction zone operated at substantially liquid-phase conversion conditions and producing a reaction zone effluent stream, with the external reaction zone being operated in a manner which allows the heat of reaction of the ongoing etherification reaction to heat the reactants present in the external reaction zone; passing the reaction zone effluent stream into the catalytic distillation zone; and, removing at least a portion of the bottoms stream from the process as a product stream.

BRIEF DESCRIPTION OF THE DRAWING

The drawing is a simplified process flow diagram showing a catalytic distillation column 2, and a close-coupled liquid-phase reaction zone 15 which discharges its effluent into the catalytic distillation column 2 via line 17.

DETAILED DESCRIPTION AND PREFERRED EMBODIMENTS

The continuous quest for more economical processes for the production of petrochemicals is driving the development of etherification and alkylation processes employing "catalytic distillation". In these processes the conversion catalyst is retained within a structure or container capable of promoting substantial vapor-liquid contact and fractional distillation concurrently with the reaction although not normally at the exact point in the apparatus. The overall apparatus normally resembles a fractionation column. This apparatus is provided with means to effect reflux and reboiling of the apparatus and normally has separate vapor-liquid contacting devices, e.g., fractionation trays devoid of catalyst in its upper and lower ends to perform the desired separations.

In the case of exothermic reactions such as alkylation, the heat released by the reaction is allowed to vaporize a portion of the reactants present in the catalytic distillation zone. This causes the more volatile reactants to concentrate in the vapor phase and pass upward through the overall apparatus while the less volatile product compound(s) flow downward in a liquid phase. This allows a facile method for separating the product from the reactants. This fractionation within the reaction zone aids in product recovery but more importantly also tends to drive the reaction to completion by removing the product compound(s) and supplying fresh reactants. A very high degree of conversion can therefore be achieved for equilibrium limited reactions by employing catalytic distillation in suitable processes including etherification, alkylation and hydration. The previously cited references describe catalytic distillation in detail.

It was suggested in the past to apply catalytic distillation to a wide variety of processes such as butene isomerization (U.S. Pat. No. 2,403,672 to M. P. Matuzak);

the hydrolysis of low molecular weight olefin oxides to produce mono-alkylene glycols (U.S. Pat. No. 2,839,588 to A. S. Parker); and the production of MTBE as described above. These early disclosures did not lead to commercialization. Catalytic distillation has only recently emerged as a commercially viable hydrocarbon conversion and petrochemical processing tool, primarily because of a legislated demand for oxygenates for motor fuel in the U.S.

Advantages attributed to the catalytic distillation concept, wherein reaction products are continuously separated from the reactants and removed from the reaction zone by fractional distillation performed concurrently with the reaction, include a decrease in the capital cost of the plant needed to perform the process, the ability to achieve a higher degree of conversion, and the ability to perform processes which formerly were performed only in a batch type operation on a continuous basis. These advantages result from performing the reaction in a separation zone capable of removing the reaction products from the reactants and catalyst. Hence it is only necessary to provide one primary vessel and the reaction is not limited by chemical equilibrium.

The preferred apparatus for retaining the catalyst in the catalytic distillation zones is described in detail in U.S. Pat. No. 5,073,236 to A. P. Gelbein which is incorporated herein by reference for its teaching as to the structure and usage of these catalyst packing systems. These devices provide a means to evenly distribute the catalyst and reactants uniformly within the desired locations in the overall vessel. The apparatus is also very effective at promoting vapor-liquid contacting and therefore fractional distillation of the product(s) from the reactants.

The reaction kinetics of olefin etherification have essentially dictated that a conventional adiabatic "prereactor" be used upstream of a catalytic distillation zone. This reactor performs a sizable amount of the conversion performed in the overall process. Attempting to perform the reaction solely in a catalytic distillation zone with a high degree of olefin conversion would require this zone to contain a large amount of catalyst. As a catalytic distillation zone contains a large amount of open space for vapor and liquid flow to promote efficient distillation, the catalyst density in a catalytic distillation zone is much lower than a conventional "packed" adiabatic bed of catalyst. The added structure required for catalytic distillation also increases the total cost per pound of installed catalyst. These effects combine to require quite large and expensive catalytic distillation reactors for etherifying olefins without a prereactor.

It is an objective of the subject invention to provide a process for the production of ethers by catalytic distillation. It is a further objective to reduce the overall size (plot size) of the catalytic distillation process unit required for the etherification of olefins. It is also an objective of the invention to eliminate the need for a prereactor during the etherification of isobutylene in a catalytic distillation zone.

These objectives are achieved by employing both a catalytic distillation and a close-coupled substantially liquid-phase adiabatic downflow reaction zone within the same overall conversion zone. The feed stream(s) enters the catalytic distillation zone at an intermediate point with catalyst above and below the feedpoint. The absence of a prereactor from the overall process can be evidenced by a lack of ethers in the feed stream(s) to the catalytic distillation zone. That is, the total mass flow of the feed streams fed into the catalytic distillation zone should be substantially free of the product ether. As some ether may possibly be present in a stream being recycled to the catalytic distillation zone, the term substantially free is intended to indicate a concentration below 1.0 mole percent and preferably below 0.5 mole percent.

The liquid phase reaction zone is "close-coupled" to the catalytic distillation zone and is part of a recycle loop returning light reactants and some products to the catalytic distillation zone. This allows the process to increase the rate of ether production from an equal amount of catalytic distillation zone packing and to reduce the height and cost of the required apparatus.

The effluent stream from the close-coupled reactor is preferably returned above the catalyst containing sections of the catalytic distillation zone. While all or some of the effluent of the close-coupled side reactor could enter the catalytic distillation zone as part of the normal reflux to the top of this zone it is greatly preferred that this effluent stream is passed into the catalytic distillation zone at a point just above the catalyst and below most of the catalyst-free fractionation devices located in the upper part of the tower. First, returning the effluent to the top of the zone would lead to the undesired presence of ethers in the overhead vapor of the zone. Second, the minimum reflux in the column is actually set by the need to recycle reactants to the catalyst containing section of the zone and this reflux rate is greater than that actually needed for effective rectification in the catalyst-free upper part of the catalytic distillation zone. By employing the side reactor effluent as reflux to the catalyst-containing section of the zone, it is possible to reduce the overhead reflux rate and to obtain the economies associated with this reduction.

It is feasible to use the side reactor effluent as reflux as there is only a small concentration of ether in this stream. This, in turn, results from the great majority of the olefin being consumed in the catalytic distillation zone.

The "close-coupled" nature of the two reaction zones used in this process is shown by a preference for a minimal pressure drop (e.g., less than 10 psia) between the exit of the close-coupled reactor and the point in the catalytic distillation zone at which it enters this zone. This pressure drop is set in part by the phase of the reactants and the point of their entrance to the catalytic distillation zone. Preferably no flow control valve is located in the connecting line. The reactants charged to the top of the liquid-phase reaction zone are restrained only by the inherent pressure drop of the closely packed catalyst employed in this zone and associated conduits. The reactants, which are slightly pressurized by a pump in the overhead system, enter the upper end of the reactor at a pressure about 5-15 psig above that present in the catalytic distillation zone. The temperature at the inlet of the liquid phase reactor is closely controlled to maintain substantially liquid phase conditions. The presence of light reactants can lead to some limited vaporization.

The subject process employs two beds of catalyst within the catalytic distillation zone. Preferably these beds will be separated from each other by one or more fractionation trays which facilitate the even distribution of the entering feed stream(s) across the internal volume of the zone. The upper and lower beds could adjoin one another as the catalyst is retained in means which should promote some admixture of vapor and liquid with the column, but this is believed to be undesirable. The point at which the feed stream enters the catalytic distillation column is intended to indicate the dividing point between the two beds.

In the subject process the upper catalyst bed is considerably larger than the lower catalyst bed. The amount of catalyst in the upper bed may range from about 50 to about 90 wt. percent, preferably 70 to 90 wt. percent of the total catalyst present in the catalytic distillation column. The upper catalyst zone preferably contains over four times as much catalyst as the lower catalyst zone. This relative amount is not based upon any consideration of the catalyst present in the close-coupled or side reactor.

The etherification reaction is quite exothermic. The liquid-phase reactor is operated in a substantially adiabatic condition and therefore the reactants are heated as they pass downward through the reaction zone. This is employed beneficially in the subject process as the heat of reaction is useful in promoting the partial vaporization of the material flowing into the catalytic distillation zone and minimizes any disruption in the temperature profile of the catalytic distillation zone without requiring any external heat exchange.

The majority of the discussion herein is directed to the preferred embodiment of isobutylene etherification. However, as those skilled in the art will recognize the invention is not so limited. The process of the subject invention can be applied in general to any reaction which is amendable to catalytic distillation and which is plagued by a slow reaction rate or other causes of low conversion. The undesired slow reaction rate can be attributable to the rate of reaction itself or to another closely related factor such as a diffusional resistance which limits the rate of reaction. A prime example of this is the hydration of olefinic hydrocarbons which is believed to be controlled to a great extent by the low mutual solubilities of the hydrocarbon and water phases.

Referring now to the Drawing, a feedstream comprising an admixture of methanol and C$_4$ hydrocarbons including isobutylene, isobutane and n-butane enters the process through line 1. The feedstream enters a catalytic distillation zone 2 at a point located between a large upper bed 5 and a small lower bed 4 of catalyst-retaining packing material. The catalytic distillation zone itself is composed of a lower fractionation zone containing a plurality of vapor-liquid contacting or fractionation trays 3, a central section comprising the two beds 4 and 5 containing a resin-type catalyst retained in the preferred packing structure and an upper fractionation zone containing an additional plurality of fractionation trays 3. These different zones are enclosed by a cylindrical upright tower. The feed stream of line 1 is preferably passed onto one of the fractionation trays 3 located between the two catalyst beds in order to distribute the reactants across the internal cross section of the tower. The feed stream could be passed, if desired, directly into contact with packing material containing the catalyst.

The fractional distillation activity which occurs within the catalytic distillation zone results in the concentration of the product ether into the liquid phase material which travels downward through the column-like zone and eventually is removed as the bottoms stream carried by line 7. A reboiler not shown is used to provide heat and vapor at the bottom of the column.

The lighter components of the feed and reactant streams rise upward through the catalytic distillation column and ascend into the intermediate zone of this apparatus containing the catalyst. While in contact with the catalyst, methanol and isobutylene react to form the desired MTBE. Fractionation of the various compounds occurs within this packed catalyst retaining zone resulting in the product ether descending downward. The feed methanol and olefins continue to rise upward through the overall apparatus at the conditions which are preferred for its operation. The material exiting the top of the uppermost catalyst retaining zone will contain an admixture of the alcohol, olefin and product ether.

The fractionation trays or other fractional distillation material such as packing located in the top of the catalytic distillation column performs an additional separation as required to remove essentially all of the product ether from the vapor phase material which is withdrawn from the top of the zone 5. This produces a vapor phase net overhead stream which should be essentially free of the product ether but will contain inert materials, such as C$_4$ paraffins, present in the feedstream which pass through the reaction zone and are not converted therein. These inert materials together with the methanol and remaining C$_4$ isoolefins present in the overhead stream are condensed in the overhead condenser 9 and collected as liquid phase material in the overhead receiver 10.

A stream of liquid phase overhead material is removed from the receiver through line 11 and divided into a first portion returned to the upper end of the catalytic distillation zone 2 through line 14 as reflux. A second portion of the overhead liquid of line 11 is removed through line 12 as a net overhead product removed as a drag stream for the purpose of eliminating from the process any inert paraffinic hydrocarbons present in the feedstream of line 1.

A third portion of the overhead liquid is diverted through line 13 and warmed in a heat exchanger not shown to a desired etherification temperature. This stream, which is preferably at a higher pressure than the fractional distillation column 2 due to passage through a pump (not shown), is fed into an upper end of a packed plug flow liquid phase etherification reactor 15. This adiabatic reactor contains a bed 16 of acidic resin catalyst. The contacting of the methanol and olefinic hydrocarbons present in the overhead liquid with the catalyst results in an additional amount of the desired product MTBE being formed. The effluent of the reactor 15 is removed via line 17 and passed directly into the catalytic distillation column 2. Preferably, this is done at a point above both catalyst beds but as shown on the Drawing a portion or all of the effluent of the side reactor 15 may be passed into the catalytic distillation column 5 at other points such as into the upper catalyst bed via optional line 18. In this manner, the unreacted feed components present in the overhead stream are exposed to a larger quantity of catalyst and are brought down to a lower point in the apparatus which allows their upward passage as vapor.

The etherification embodiment of the subject process consumes two different reactants. The first is one or more C$_4$-C$_6$ tertiary olefin such as isobutylene, an isoamylene (C$_5$H$_{10}$), or isohexylene (C$_6$H$_{12}$). It is contemplated that in the normal commercial application of the subject process these olefinic reactants, which are branched at the double bond, will be present in a mixture of other branched and straight chain olefinic hydrocarbons having the same number of carbon atoms per molecule. Therefore, a preferred feed olefin, such as isoamylene, will normally be present in the feed stream in admixture with one or more amylene isomers: 1-pentene, (n-propylethylene); 2-pentene, (sym-ethylethylethylene); 2-Me-1 butene, (unsym-methylethylethylene); 2-Me-2-butene, (trimethy-ethylene); and 3-Me-1-butene (isopropylethylene). The expected olefin feed streams to the subject process will normally be derived from a fluid catalytic cracking (FCC) reaction zone, a thermal cracker or similar large scale refining process and are expected to contain a mixture of all of the possible $C_5$ or $C_6$ isomers in an approximate equilibrium concentration. The olefin feed stream also can be derived from the effluent of a dehydrogenation process. The feed or effluent to this process may be fractionated to result in a product containing only molecules having the same number of carbon atoms. This olefin stream could be further purified as by adsorptive separation to yield a high purity isoolefin feed stream.

The second reactant consumed in the subject process is a $C_1$ or $C_2$ alcohol, that is methanol or ethanol although heavier alcohols such as isopropanol or isobutanol could be consumed. The product hydrocarbon can therefore be one of a wide variety of $C_5$–$C_8$ ethers including tertiary amyl methyl ether(TAME), tertiary-amyl ethyl ether, tertiary-amyl propyl ether, tertiary-amyl n-butyl ether, and tertiary hexyl methyl ether (THME).

While some of the higher boiling ethers resulting from the reaction of these reactants may not be suitable for use in gasoline, they may be useful in diesel fuel, jet fuel or other fuels or as feed stocks in petrochemical processes or as end product petrochemicals having their own utility.

The subject process can be practiced with any suitable catalysts. This may be any heterogeneous catalyst which gives satisfactory performance in terms of conversion and selectivity for the desired reaction at the conditions required to allow fractional distillation of the reactants and products. The best catalysts to employ in the subject process will of course to a great extent depend upon the identity of the specific reactants to be converted in the process. It is contemplated that different catalysts could be employed in the catalytic distillation reaction zone and in the liquid-phase reaction zone.

The subject invention is not limited to any particular catalyst composition or structure. The presently preferred catalysts are the previously referred to acidic resin catalysts, but other catalysts can be utilized in the process including zeolitic catalysts comprising beta zeolite, Y zeolite or a titania or zirconia oxide treated with sulfuric acid as per European Patent Publication 506 428-A1.

The preferred etherification catalyst is a macroporous acid form sulfonic ion exchange resin such as the sulfonated styrene-divinylbenzene resin as described in U.S. Pat. No. 2,922,822 having a degree of crosslinking of from about 5 to 60%. Suitable resins are available commercially. Specialized resins have been described in the art including copolymers of sulfonyl fluorovinyl ether and fluorocarbons as described in U.S. Pat. Nos. 3,784,399 and 3,849,243 Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 m$^2$/g, a pore volume of 0.6-2.5 ml/g and a mean pore diameter of 40-1000 angstroms. A particularly suitable and preferred catalyst is sold under the designation Amberlyst 15 and Amberlyst 35 by Rohm & Haas.

It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679.

It is also contemplated that nonresin etherification catalysts can be employed in the subject process. For instance U.S. Pat. Nos. 5,214,217 and 5,214,218 disclose zeolitic and treated clay based catalysts and European Patent Publication 528628 based on application 93-060453/08 disclosed an HF modified Y zeolite catalyst.

Various etherification process techniques, reaction conditions and product recovery methods are described in U.S. Pat. No. 4,219,678 to Obenous et al. and U.S. Pat. No. 4,282,389 to Droste et al. which are incorporated herein for this teaching.

There are many possible variations to the process embodiment shown in the Drawing. For instance the feed stream of line 1 may be charged to the catalytic reaction zone at other points than shown in the drawing. An internal overhead condenser can be employed instead of an external condenser. Other possible variations relate to the construction of the vapor-liquid contacting and catalyst retention devices employed in the process. The Drawing illustrates the use of fractionation trays. These may be any suitable type of tray with a sieve tray having a conventional downcomer arrangement being suitable. Another suitable type of fractionation tray is referred to as a Multiple Downcomer tray. This type of tray is described in U.S. Pat. No. 3,410,540. Those portions of the overall vessel devoted to fractionation can alternatively contain structured or dumped packing material and suitable liquid distributors. These devices provide a means to evenly distribute the catalyst within the desired locations in the vessel and also are effective in promoting vapor-liquid contacting.

While a structured catalyst retention device resembling structured column packing is preferred, there are other methods of retaining catalyst within the column which should also prove effective. For instance it is known that the catalyst may be retained upon the surface of perforated or sieve trays by the use of screens or bags or other particle retention means. It is also known that catalyst may be retained within downcomers used to convey liquid between fractionation trays.

While it is preferred that catalyst is present only in the central catalyst retaining section the process may be practiced with other configurations including the distribution of catalyst along the height of the catalytic distillation zone or column.

Temperatures which are suitable for use in the subject process are essentially the same as those employed in a conventional etherification process. The combination of temperature and pressure must be selected to maintain only a portion of the compounds in the catalytic distillation zones present as liquids since the etherification reaction is a liquid phase reaction and vapor is needed for distillation. Vapor is desired only as necessary to effect distillation. Suitable temperatures are generally from about 30° to about 140° C. especially from about 50° to about 100° C. Pressures which are suitable for use herein preferably are above about 1 atmosphere but should not be in excess of about 130 atmospheres. An especially desirable pressure range is from about; 1.2 to about 20 atmospheres. The concept of space velocity does not apply to catalytic distillation. The reactants should be fed to the vessel in the proper stoichiometric ratio at a rate equal to their rate of consumption therein, which is most easily measured by monitoring the rate of ether production.

The close-coupled adiabatic reaction zone, which does not employ catalytic distillation, is preferably maintained at an inlet temperature of 40°–100° C. and a pressure sufficient to maintain at least most, preferably over 90%, of the reactive olefins in a liquid phase. A pressure of from 1.2 to 30 atmospheres is preferred.

The operation of the subject invention may be illustrated by the following example which is based upon engineering design work and computer simulations verified by modeling prior art processes and test equipment. The feedstream of line 1 would contain approximately 300 moles per hour methanol and 1325 moles per hour of a mixed paraffin/olefin $C_4$ stream. This feed admixture would be passed into the fractional distillation zone 2. This zone would contain about 16 sieve-type trays in the lower portion of the column and about 11 trays in the upper portion of the column. The preferred structural packing referred to above would be present in the catalyst beds located in the intermediate portion of the column between these trayed sections of the zone. This portion of the column would contain approximately 1760 cubic meters of the catalyst-containing packing material. The catalytic distillation column 2 would be operated at conditions which include a temperature of approximately 68 degrees Centigrade and 121 psia (834 kpa), with these conditions being measured at a central location within the upper catalyst retention media 5. The overhead stream of line 6 would have a flow rate of approximately 261,516 lbs per hour (118,728 kg/hr) and would be cooled to a temperature of approximately 60 degrees Centigrade to effect its condensation. Approximately 123,876 lbs per hour (56,189 kg/hr) of this material would be returned to the upper portion of column 2 as reflux. A portion of the overhead liquid equal to about 68821 lb per hour (31,217 kg/hr) would be withdrawn as the dragstream or net overhead product via line 12 with the remainder of this material being passed into the close-coupled side reactor 15. The closed coupled side reactor would be operated at an inlet pressure of about 130 psia (896 kPa) and an inlet temperature of about 43 degrees Centigrade. The effluent of this close-coupled reactor 15 is expected to have a temperature of approximately 44 degrees Centigrade and contain 204 lb/hr (92 kg/hr) of MTBE. This effluent stream is returned to the catalytic distillation zone at a point one tray above the catalyst-containing package. The net overhead liquid stream of line 12 will have a concentration of approximately 4.2 wt. percent methanol, and 95.6 wt. percent unreactive $C_4$ olefins and paraffins. The overhead will also contain about 0.2% reactive olefins. The net overhead stream may be passed to a waterwash column or other appropriate equipment for the recovery of the methanol. The net bottoms stream of line 7 will contain approximately 18,346 lbs per hour (8,329 kg/hr) of MTBE.

The subject process can be used to perform reactions other than etherification. These reactions include esterification and olefin hydration reactions. Of these two reactions, hydration to produce alcohols suitable for use in motor fuels is the most desirable. Further, as described in U.K. Patent Application 2 187 741 A, water may be added during etherification to coproduce an alcohol during etherification.

The hydration of olefinic hydrocarbons can be performed at known conditions using conventional acidic resin catalysts in a catalytic distillation column. Hydration conditions in general would include a temperature of from 40 to 150 degrees Centigrade, preferably 40 to 60 degrees Centigrade, and a pressure of from about 26 to 500 psig (180–3450 kPa). In general the hydration conditions would be quite similar to those employed in etherification. The hydration and etherification of olefins to produce motor fuel blending components is described in U.S. Pat. Nos. 4,886,918 and 4,935,552 and in European Patent Application 0451989A1 which are incorporated herein by reference for their teaching of suitable reaction conditions, feedstocks and operation.

One embodiment of the subject invention is therefore a process for the hydration of olefinic hydrocarbons to form a corresponding alcohol. Water would therefore be charged to the process as a feed compound. Examples of the alcohols which could be produced include tertiary butyl alcohol, tertiary amyl alcohol and tertiary hexyl alcohol. The process of the subject invention can also be employed in a process wherein both ethers and alcohols are produced or in a process for the sequential production of an alcohol followed by its conversion to an ether. It is therefore contemplated that diisopropylether could be produced by first hydrating propylene and then reacting the resultant isopropyl alcohol with additional propylene. This would be performed using two or more separation reaction zones.

The subject hydrocarbon conversion process can also be applied to other additive type reactions such as alkylation. This includes the alkylation of paraffins including isobutane and the alkylation of aromatic hydrocarbons including benzene and toluene. The former reaction can be used to produce motor fuel while the latter can be used to produce ethyl benzene, isopropyl benzene, dialkylbenzenes or heavier $C_{15}$–$C_{30}$ linear alkylbenzenes suitable for use in detergent manufacture. The reactant added to these substrate hydrocarbons may be either a $C_2$–$C_{20}$ olefin or an olefin-acting compound such as a light alcohol, e.g., methanol or ethanol.

These alkylation reactions are preferably promoted by a solid acid catalyst. Examples of some acid materials which can be employed in these catalysts are amorphous silica-alumina, fluoride treated silica-alumina, fluoride treated alumina, acid resins, Y zeolites and dealuminated Y zeolites, ZSM-5 zeolites, beta zeolites, omega zeolite and silicalite. Suitable alkylation catalysts are described in U.S. Pat. Nos. 4,469,908; 4,489,214; 4,459,426 and 4,365,104 which are incorporated herein for their teaching as to catalyst formulation and reaction conditions.

Processes for alkylation via catalytic distillation have been described in the open literature including U.S. Pat. Nos. 4,935,577; 5,082,990; 5,019,669 and 4,849,569. These patents are incorporated herein for their teaching as to the performance of alkylation in a catalytic distillation reaction zone.

Alkylation zones employed in the subject process will be operated at conditions which preferably maintain at least a portion of the reactants and a majority of the product hydrocarbons present in a liquid phase while in contact with the catalyst. Alkylation reactions can be performed over an extremely wide range of conditions including a temperature of from about 0 to 200 degrees Centigrade, preferably from 20 to 150 degrees C., and a pressure of atmospheric to 500 psig, preferably from 20 to 200 psig (1380 kpa).

One embodiment of the subject invention may therefore be characterized as a hydrocarbon conversion process which comprises the steps of passing a feed stream comprising a first reactant and a second reactant into a catalytic distillation zone comprising upper and lower fractionation sections and a central catalytic distillation section comprising upper and lower catalyst beds and maintained at mixed-phase conversion conditions which are effective to promote both the exothermic reaction of the first and second reactants to form a product compound and fractional distillation of the contents of the catalytic distillation zone into an overhead vapor stream comprising the first and second reactants and a bottoms stream which is rich in the product compound which is less volatile than either the first or the second reactants, with the feed stream entering the catalytic distillation zone between the upper and lower catalyst beds; condensing the overhead vapor stream to produce an overhead liquid, passing a first portion of the overhead liquid into the catalytic distillation zone as reflux and removing a second portion of the overhead liquid as a net overhead product; passing a third portion of the over,-head liquid into an external reaction zone operated at liquid-phase conversion conditions and producing a reaction zone effluent stream, with the external reaction zone being operated in a manner which allows the heat of reaction of the ongoing reaction to heat the reactants present in the external reaction zone; passing an effluent stream removed from the external reaction zone into the catalytic distillation zone at a point just above the upper catalyst bed; and, removing at least a portion of the bottoms stream from the process as a product stream.

The subject conversion process can be used as a separate process unit or as part of an integrated complex. In such an integrated complex any hydrocarbons which are not reacted in the process, such as isobutane present in the feed stream used to produce MTBE, can be recycled to a dehydrogenation unit for the production of additional isobutylene or passed into a different reaction zone.

While it is presently preferred that the different reactors (the catalytic distillation zone and the close-coupled or side reactor) contain the same catalyst, there is no absolute requirement for this. The close-coupled reactor 15 may therefore contain a different catalyst than the catalytic distillation zone 2. Different catalysts may also be used in beds 4 and 5. For instance, the different reactant concentrations and somewhat different reaction zone operating conditions may make different catalysts more effective or selective in promoting the desired reaction. It is also contemplated that two or more catalysts having totally different functions could be employed within the process. For instance, the close-coupled reaction zone or the catalytic distillation zone may contain an olefin skeletal or double bond isomerization catalyst or an olefin hydration catalyst in addition to the etherification catalyst. The catalysts could be present as a physical admixture or in separate layers or zones distributed in different regions of either reactor. The reaction zones may employ an admixture of a resin etherification catalyst and a zeolitic isomerization catalyst. One or both of the reaction zones may also contain a catalyst containing a nonzeolitic molecular sieve (NZMS) as described in U.S. Pat. Nos. 4,864,068 and 5,114,563.

What is claimed:

1. A process for the production of ethers which comprises the steps:

(a) passing at least one $C_4$ to $C_6$ isoolefin and a $C_1$ or $C_2$ alcohol into a catalytic distillation zone maintained at mixed-phase conversion conditions which are effective to promote both the exothermic reaction of said isoolefin and alcohol to form a product ether and the fractional distillation of the contents of the catalytic distillation zone into an overhead vapor stream comprising said isoolefin and said alcohol and a bottoms stream which is rich in the product ether, with said isoolefin and said alcohol first entering the catalytic distillation zone at a point intermediate upper first and lower second catalyst retaining zones located within the catalytic distillation zone;

(b) condensing the overhead vapor stream to produce an overhead liquid and passing a first portion of the overhead liquid into the catalytic distillation zone as reflux;

(c) passing a second portion of the overhead liquid into an external reaction zone operated at liquid-phase conversion conditions and producing a reaction zone effluent stream, with the external reaction zone being operated in a manner which allows the heat of reaction of the ongoing etherification reaction to heat the reactants present in the external reaction zone;

(d) passing the reaction zone effluent stream into the catalytic distillation zone; and, (e) removing at least a portion of the bottoms stream from the process as a product stream.

2. The process of claim 1 wherein the reaction zone effluent stream is passed into the catalytic distillation zone at a point above said upper first catalyst retaining zone.

3. The process of claim 1 wherein the product ether is methyl tertiary butyl ether.

4. The process of claim 1 wherein the product ether is tertiary amyl methyl ether.

5. The process of claim 1 further characterized in that the isoolefin and alcohol are fed to the catalytic distillation zone as part of a feed stream which contains less than 1 mole percent ethers.

6. The process of claim 1 further characterized in that the upper first bed of catalyst contains over twice as much catalyst as the lower second bed of catalyst.

7. A process for the production of ethers which comprises the steps:

(a) passing $C_4$ or $C_5$ isoolefin and a $C_1$ or $C_2$ alcohol into a catalytic distillation zone maintained at mixed-phase conversion conditions which are effective to promote both the exothermic reaction of said isoolefin and alcohol reactants to form a product ether and the fractional distillation of the contents of the catalytic distillation zone into an overhead vapor stream comprising said isoolefin and said alcohol and a bottom stream which is rich in the product ether, with said isoolefin and said alcohol being substantially free of any ether and entering the catalytic distillation zone at a point intermediate upper first and a lower second catalyst retaining zones located within the catalytic distillation zone; with the first catalyst retaining zone containing over four times as much catalyst as the second catalyst retaining zone;

(b) condensing the overhead vapor stream to produce an overhead liquid, passing a first portion of the overhead liquid into the catalytic distillation zone as reflux and removing a second portion of the overhead liquid as a net overhead product;

(c) passing a third portion of the overhead liquid into an external reaction zone operated at substantially liquid-phase conversion conditions and producing a reaction zone effluent stream, with the external reaction zone being operated in a manner which allows the heat of reaction of the ongoing reaction to heat the reactants present in the external reaction zone;

(d) passing an effluent stream removed from the external reaction zone into the catalytic distillation zone; and, (e) removing at least a portion of the bottoms stream from the process as an ether-containing product stream.

8. The process of claim 7 wherein at least a portion of the external reaction zone effluent stream is passed into the catalytic distillation zone at a point above said upper first bed of catalyst.

9. The process of claim 7 wherein the product ether is methyl tertiary butyl ether.

10. The process of claim 7 wherein the product ether is tertiary amyl methyl ether.

11. The process of claim 7 further characterized in that the feed stream contains less than 1 mole percent ethers.

12. A process for the production of ethers which comprises the steps:

(a) passing a feed stream which is substantially free of ethers and which comprises at least one $C_4$ or $C_5$ isoolefin and a $C_1$ or $C_2$ alcohol into a catalytic distillation zone maintained at mixed-phase conversion conditions which are effective to promote both the exothermic reaction of said isoolefin and alcohol to form a product $C_5$-plus ether and the fractional distillation of the contents of the catalytic distillation zone into an overhead vapor stream comprising said isoolefin and said alcohol and a bottoms stream which is rich in the product ether, with the feed stream entering the catalytic distillation zone at a point intermediate upper first and lower second catalyst retaining zones located within the catalytic distillation zone, with the first catalyst retaining zone containing over four times as much catalyst as the lower second catalyst retaining zone;

(b) condensing the overhead vapor stream to produce an overhead liquid, passing a first portion of the overhead liquid into the catalytic distillation zone as reflux and removing a second portion of the overhead liquid as a net overhead product;

(c) passing a third portion of the overhead liquid into an external reaction zone operated at substantially liquid-phase conversion conditions and producing a reaction zone effluent stream, with the external reaction zone being operated in a manner which allows the heat of reaction of the ongoing reaction to heat the reactants present in the external reaction zone;

(d) passing an effluent stream removed from the external reaction zone into the catalytic distillation zone at a point above all catalyst present in the catalytic distillation zone; and, (e) removing at least a portion of the bottoms stream from the process as a product stream.

13. The process of claim 12 wherein the product ether is methyl tertiary butyl ether.

14. The process of claim 12 wherein the product ether is tertiary amyl methyl ether.

* * * * *